(12) United States Patent
Petersen et al.

(10) Patent No.: US 7,371,408 B1
(45) Date of Patent: *May 13, 2008

(54) BONE GRAFT SUBSTITUTE COMPOSITION

(75) Inventors: Donald W. Petersen, Lakeland, TN (US); Warren O. Haggard, Bartlett, TN (US); Donald A. Randolph, Wheaton, IL (US); Cary P. Hagan, Germantown, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 637 days.

This patent is subject to a terminal disclaimer.

(21) Appl. No.: 09/327,761

(22) Filed: Jun. 7, 1999

(51) Int. Cl.
*A61K 35/32* (2006.01)

(52) U.S. Cl. ...................... 424/549; 424/682; 424/696; 623/16.11; 623/23.51; 623/23.61; 623/23.62; 623/23.63

(58) Field of Classification Search ................ 424/433, 424/423, 426, 549, 696
See application file for complete search history.

(56) References Cited

U.S. PATENT DOCUMENTS

| | | |
|---|---|---|
| 4,430,760 A | 2/1984 | Smestad |
| 4,568,536 A | 2/1986 | Kronenthal et al. |
| 4,595,713 A | 6/1986 | St. John |
| 4,596,574 A | 6/1986 | Urist |
| 4,612,009 A | 9/1986 | Drobnik et al. |
| 4,619,655 A * | 10/1986 | Hanker et al. ............ 623/23.61 |
| 4,650,665 A | 3/1987 | Kronenthal et al. |
| 4,681,763 A | 7/1987 | Nathanson et al. |
| 4,820,306 A | 4/1989 | Gorman et al. |
| 4,880,660 A | 11/1989 | Aasen et al. |
| 4,882,149 A | 11/1989 | Spector |
| 4,892,734 A | 1/1990 | Leonard |
| 4,975,526 A | 12/1990 | Kuberasampath et al. |
| 4,994,030 A | 2/1991 | Glowezewskie et al. |
| 5,061,286 A | 10/1991 | Lyle |
| 5,073,373 A | 12/1991 | O'Leary et al. |
| 5,147,403 A | 9/1992 | Gitelis |
| 5,162,114 A | 11/1992 | Kuberasampath et al. |
| 5,219,897 A | 6/1993 | Murray |
| 5,236,456 A | 8/1993 | O'Leary et al. |
| 5,236,971 A | 8/1993 | Murray |
| 5,264,214 A | 11/1993 | Rhee et al. |
| 5,284,655 A | 2/1994 | Bogdansky et al. |
| 5,290,558 A | 3/1994 | O'Leary et al. |
| 5,298,254 A | 3/1994 | Prewett et al. |
| 5,306,304 A | 4/1994 | Gendler |
| 5,314,476 A | 5/1994 | Prewett et al. |
| 5,320,844 A | 6/1994 | Liu |
| 5,336,699 A | 8/1994 | Cooke et al. |
| 5,366,507 A | 11/1994 | Sottosanti |
| 5,385,887 A | 1/1995 | Yim et al. ..................... 514/12 |
| 5,405,390 A | 4/1995 | O'Leary et al. |
| 5,417,975 A | 5/1995 | Lussi et al. |
| 5,425,769 A * | 6/1995 | Snyders, Jr. .................. 623/16 |
| 5,439,684 A | 8/1995 | Prewett et al. |
| 5,462,722 A | 10/1995 | Liu et al. |
| 5,482,551 A | 1/1996 | Morris et al. |
| 5,484,601 A | 1/1996 | O'Leary et al. |
| 5,507,813 A | 4/1996 | Dowd et al. |
| 5,510,396 A | 4/1996 | Prewett et al. |
| 5,512,610 A | 4/1996 | Lin |
| 5,531,791 A | 7/1996 | Wolfinbarger, Jr. |
| 5,569,308 A | 10/1996 | Sottosanti |
| 5,573,771 A | 11/1996 | Geistich et al. |
| 5,578,662 A | 11/1996 | Bennett et al. |
| 5,614,206 A * | 3/1997 | Randolph et al. ........... 424/426 |
| 5,618,549 A | 4/1997 | Patat et al. |
| 5,676,146 A | 10/1997 | Scarborough |
| 5,681,873 A | 10/1997 | Norton et al. |
| 5,697,981 A | 12/1997 | Ison et al. |
| 5,700,289 A | 12/1997 | Breitbart et al. |
| 5,707,962 A | 1/1998 | Chen et al. |
| 5,727,945 A | 3/1998 | Dannenbaum |
| 5,756,127 A * | 5/1998 | Grisoni et al. .............. 424/489 |
| 5,763,416 A | 6/1998 | Bonadio et al. |
| 5,766,618 A | 6/1998 | Laurencin et al. |
| 5,769,897 A | 6/1998 | Harte |
| 5,788,976 A | 8/1998 | Bradford |
| 5,807,567 A | 9/1998 | Randolph et al. |
| 5,824,087 A | 10/1998 | Aspden et al. |
| 5,830,493 A | 11/1998 | Yokota et al. |
| 5,861,445 A | 1/1999 | Xu et al. |
| 5,899,939 A | 5/1999 | Boyce et al. |
| 5,910,315 A | 6/1999 | Stevenson et al. |
| 5,948,426 A | 9/1999 | Jefferies |
| 5,948,428 A | 9/1999 | Lee et al. |
| 5,964,805 A | 10/1999 | Stone |
| 5,972,368 A | 10/1999 | McKay |
| 5,981,828 A | 11/1999 | Nelson et al. |
| 6,030,635 A * | 2/2000 | Gertzman et al. .......... 424/423 |
| 6,030,636 A | 2/2000 | Randolph et al. |

(Continued)

FOREIGN PATENT DOCUMENTS

DE        196 20 117 C1     7/1997

(Continued)

OTHER PUBLICATIONS

Sidqui et al., Biomaterials 16(17): 1327-1332 (1995). Abstract.*

(Continued)

*Primary Examiner*—Leon B. Lankford, Jr.
*Assistant Examiner*—Allison M. Ford
(74) *Attorney, Agent, or Firm*—Alston & Bird LLP

(57) ABSTRACT

A bone graft substitute composition comprising calcium sulfate; a mixing solution selected from the group consisting of sterile water, sodium chloride, phosphate buffered saline, potassium chloride, and sodium sulfate; and a plasticizing substance selected from the group consisting of carboxymethylcellulose, polyvinyl alcohol, methycellulose, and hydroxypropyl methylcellulose.

16 Claims, No Drawings

U.S. PATENT DOCUMENTS

| | | | |
|---|---|---|---|
| 6,037,519 A | 3/2000 | McKay | |
| 6,051,247 A | 4/2000 | Hench et al. | |
| 6,056,970 A | 5/2000 | Greenawalt et al. | |
| 6,071,530 A | 6/2000 | Polson et al. | |
| 6,083,522 A | 7/2000 | Chu et al. | |
| 6,118,043 A | 9/2000 | Nies et al. | |
| 6,224,635 B1* | 5/2001 | Ricci et al. | 623/23.62 |
| 2002/0016636 A1* | 2/2002 | Ricci et al. | 623/23.51 |

FOREIGN PATENT DOCUMENTS

| | | |
|---|---|---|
| GB | 2 093 348 A | 9/1982 |
| WO | WO 89/04646 A1 | 6/1989 |
| WO | WO 96/39203 | 12/1996 |
| WO | WO 98/40113 | 9/1998 |
| WO | WO 99/15150 A1 | 4/1999 |

OTHER PUBLICATIONS

Hanker, et al., "Setting of Composite Hydroxylapatite/Plaster Implants with Blood for Bone Reconstruction," *Proceedings of the 44th Annual Meeting of the Electron Microscopy Society of America*, Copyright 1986.

Advances in Biomaterials for Bone Regeneration, Orthopedics, vol. 26, No. 5/Supplement, May 2003.

Randal R. Betz, M.D., "Limitations of Autograft and Allograft: New Synthetic Solutions", Orthopedics, vol. 25, No. 5, Supplement May 2002.

"Bone Graft Substitutes Safe, Effective", AMA Science News Media Briefings, Dec. 6, 2001.

Turner et al., "Radiographic and Histologic Assessment of Calcium Sulfate in Experimental Animal Models and Clinical use as a Resorbable Bone-Graft Substitute, A Bone-Graft Expander, and a Method for Local Antibiotic Delivery", The Journal of Bone and Joint Surgery, Incorporated, vol. 83-A, Supp. 2, Part 1, 2001.

Greenwald et al., "Bone-Graft Substitutes: Facts, Fictions, and Applications", The Journal of Bone & Joint Surgery, JBJS Org., vol. 83-A, Supplement 2, Part 2, 2001.

Evelyn B. Kelly, Ph.D., "New Frontiers in Bone Grafting", Orthopaedic Technology Review, vol. 2, No. 9, Oct. 2000.

Adkisson et al., "Rapid Quantitative Bioassay of Osteoinduction", Journal of Orthopaedic Research, 18:503-511, 2000.

Biomaterials Tutorial, www.btec.cmu.edu/tutorial/biomaterials/biomaterials.htm, undated.

Grimandi, G., "In vitro evaluation of a new injectable calcium phosphate material", *J. Biomed Mater Res.*, 1998, pp. 660-666, vol. 39.

* cited by examiner

BONE GRAFT SUBSTITUTE COMPOSITION

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates, in general, to bone graft substitute compositions.

2. Information Disclosure Statement

Calcium sulfate has been clinically used for many years as a bone void filler with successful results.

A preliminary patentability search produced the following patents which appear to be relevant to the present invention:

Hanker et al., U.S. Pat. No. 4,619,655, issued Oct. 28, 1986, discloses an animal implant comprising a scaffold material composed of plaster of Paris and a non-bioresorbable calcium material (such as calcium phosphate ceramic particles) bound with the plaster of Paris; a method of inserting such a composition in fluid or semisolid form into the appropriate body location of an animal (e.g., about a fracture locus); and a method of inserting a preform of such composition into the appropriate location of an animal (e.g., at the locus of a fracture).

Gitelis, U.S. Pat. No. 5,147,403, issued Sep. 15, 1992, discloses a method or technique for implanting a prosthesis comprising the steps of first preparing the surface of a bone to receive the prosthesis, then applying a calcium sulfate suspension in free flowing form to the prepared bone surface, and then seating the prosthesis to the coated bone surface.

Randolph, U.S. Pat. No. 5,614,206, issued Mar. 25, 1997, and U.S. Pat. No. 5,807,567, issued Sep. 15, 1998, disclose processes for preparing pellets by mixing of calcium sulfate, water and other medicaments to provide controlled release of calcium sulfate and medicaments.

Snyder, U.S. Pat. No. 5,425,769, issued Jun. 20, 1995, discloses a composition for an artificial bone substitute material consisting of collagen in a calcium sulfate matrix which can be rendered porous by a foaming agent. The composition is adaptable for osseous repair by adjusting the collagen and calcium sulfate in varying ratios to suit particular applications and including admixtures of growth factors.

Sottosanti, U.S. Pat. No. 5,366,507, discloses a composition for use in bone tissue regeneration, the composition containing a barrier material and a graft material. The barrier material can be calcium sulfate, while the graft material may consist of a composite graft material containing demineralized, freeze-dried, allogenic bone and calcium sulfate.

Sottosanti, U.S. Pat. No. 5,569,308, discloses a method for use in bone tissue regeneration including first filling a graft site with graft material, and then placing a layer of barrier material over at least a portion of the graft material. The barrier material can be calcium sulfate, while the graft material may consist a composite graft material containing demineralized, freeze-dried, allogenic bone and calcium sulfate.

Hanker et al, "Setting of Composite Hydroxylapatite/Plaster Implants with Blood for Bone Reconstruction," Proceedings of the 44th Annual Meeting of the Electron Microscopy Society of America, Copyright 1986, discloses using blood as the only moistening agent in a plaster or plaster/HA mixture as long as accelerator salts are utilized, and suggests that the putty-like consistency of such compositions offers distinct advantages in moldability and workability.

Osteotech, Inc., of Shrewsbury, N.J., markets a bone graft substitute under the mark Grafton®. It is comprised of demineralized bone matrix and glycerol as a carrier material. The carrier material, glycerol, is a viscous, gel-like, weak alcohol that is hydrophilic and water soluble. It is recognized by the Food and Drug Administration as a "Generally Regarded As Safe" substance.

DePuy, Inc., of Warsaw, Ind., markets a bone graft substitute under the mark DynaGraft. It is comprised of demineralized bone matrix and poloxamer as a carrier material. Poloxamer is a reverse phase polymer which becomes more viscous with increasing temperature.

Nothing in the known prior art discloses or suggests the present invention. More specifically, nothing in the known prior art discloses or suggests a bone graft substitute composition including calcium sulfate, a mixing solution such as sterile water, and a plasticizing substance such as carboxymethylcellulose, and having an extended set time and sufficient robustness to withstand fluid impact with minimal erosion.

BRIEF SUMMARY OF THE INVENTION

A basic concept of the present invention is to provide bone graft substitute composition having an extended set time and sufficient robustness to withstand fluid impact with minimal erosion for expanded clinical applications.

The bone graft substitute composition of the present invention comprises, in general, calcium sulfate; a mixing solution such as sterile water; and a plasticizing substance such as carboxymethylcellulose.

One object of the present invention is to provide a bone graft substitute composition that can be mixed into a paste and then loaded into a syringe and ejected for an extended period of time (e.g., more than ten minutes).

Another object of the present invention is to provide a bone graft substitute composition that can be mixed into a putty and then handled and formed into desired shapes for an extended period of time (e.g., more than ten minutes).

BRIEF DESCRIPTION OF THE SEVERAL VIEWS OF THE DRAWINGS

Not Applicable.

DETAILED DESCRIPTION OF THE INVENTION

The bone graft substitute composition of the present invention comprises, in general, a quantity of calcium sulfate, a quantity of fluid (e.g., sterile water), and a quantity of a plasticizing substance (e.g., carboxymethylcellulose) which provides a resultant composition that is robust and has an extended set time. The extended set time of the resultant composition provides a useful working time of at least 10 minutes to allow sufficient time for a surgeon to properly apply the bone graft substitute composition, while the robustness of the resultant composition allows the implanted composition to withstand the typical pressure of body fluids, irrigation fluids and/or suctioning with minimal material erosion, disintegration or dissolution.

The bone graft substitute composition of the present invention may comprise a mixture of calcium sulfate; a mixing solution selected from the group consisting of sterile water, inorganic salts, and cationic surface active agents including sodium chloride, phosphate buffered saline, potassium chloride, sodium sulfate, potassium sulfate, EDTA, ammonium sulfate, ammonium acetate, and sodium acetate, etc.; and a plasticizing substance selected from the group consisting of cellulose derivatives including sodium carboxymethylcellulose, methycellulose, hydroxypropyl methylcellulose, ethylcellulose, hydroxethylcellulose and cellulose acetate butyrate, and higher molecular weight alcohols including glycerol and vinyl alcohols, etc. The bone graft substitute composition may include demineralized bone matrix. One formulation of the composition may be approximately 100 parts calcium sulfate by weight, 11.1 parts carboxymethylcellulose by weight, 185.2 parts water by weight, and 69.4 parts demineralized bone matrix by weight. Another formulation of the composition may be approximately 100 parts calcium sulfate by weight, 6.3 parts carboxymethylcellulose by weight, and 31 parts water by weight. Another formulation of the composition may be approximately 100 parts calcium sulfate by weight, 1.2 parts carboxymethylcellulose by weight, and 31 parts water by weight. Another formulation of the composition may be approximately 80-120 parts calcium sulfate by weight, 1-40 parts carboxymethylcellulose by weight, and 21-250 parts water by weight. The composition may include a bioactive agent selected from the group consisting of demineralized bone matrix, growth factors, hyaluronic acid, bone morphogenic proteins, bone autograft, and bone marrow, etc. The composition may include sodium bicarbonate. For example, the composition may include 0.1-2% sodium bicarbonate by weight for creating a porous structure in the resultant composition. Possible embodiments of the bone graft substitute composition of the present invention may include at least one additive selected from the group consisting of antiviral agent, antimicrobial agent, antibiotic agent, amino acid, peptide, vitamin, inorganic element, protein synthesis co-factor, hormone, endocrine tissue, synthesizer, enzyme, polymer cell scaffolding agent with parenchymal cells, angiogenic drug, demineralized bone powder, collagen lattice, antigenic agent, cytoskeletal agent, mesenchymal stem cells, bone digester, antitumor agent, cellular attractant, fibronectin, growth hormone, cellular attachment agent, immunosuppressant, nucleic acid, surface active agent, hydroxyapatite, penetration enhancer, bone allograft, and chunks, shards, and/or pellets of calcium sulfate.

Preferred Embodiment 1

An injectable bone graft substitute composition having the following preferred formulation: 100 parts by weight of medical grade calcium sulfate hemihydrate (MGCSH), 11.1 parts by weight of carboxymethylcellulose (CMC), 69.4 parts by weight of demineralized bone matrix (DBM), and 162 parts by weight of sterile water.

The preferred method for mixing this putty bone graft substitute composition comprises the following steps: (1) dry blend the powder components (i.e., the calcium sulfate hemihydrate, carboxymethylcellulose, and demineralized bone matrix); (2) add the sterile water; and (3) mix or stir all components for approximately 30 seconds to one minute or until the desired putty-like consistency is achieved.

The resultant injectable bone graft substitute composition has the following characteristic/criteria:

Handability—the resultant composition should: (a) be a single cohesive bolus; (b) be able to be handled and manipulated with minimal to no material transfer (sticking) to latex gloved hand; (c) be able to be handled without material crumbling or falling apart; and (d) exhibit minimal cracking or "tearing" with extreme manipulation, e.g., hard squeezing;

Ejectability—the resultant composition should: (a) be able to be easily manipulated, e.g., rolled into a long cylinder or other suitable shape, so as to be manually placed into an appropriate injection apparatus, e.g., a syringe; and (b) be able to be ejected through a ⅛ inch (0.3175 centimeter) diameter orifice with relatively little pressure required; and Robustness—the resultant composition, after being placed or injected into or onto the desired location, should be able to withstand body fluids, reasonable irrigation fluids and/or suctioning with minimal material erosion, disintegration or dissolution.

Preferred Embodiment 2

A putty bone graft substitute composition having the following preferred formulation: 100 parts by weight of medical grade calcium sulfate hemihydrate (MGCSH), 6.3 parts by weight of carboxymethylcellulose (CMC), and 31 parts by weight of sterile water.

The preferred method for mixing this putty bone graft substitute composition comprises the following steps: (1) dry blend the powder components (i.e., the calcium sulfate hemihydrate, and carboxymethylcellulose); (2) add the sterile water; and (3) mix or stir all components for approximately 30 seconds to one minute or until the desired putty-like consistency is achieved.

The resultant putty bone graft substitute composition has the following characteristic/criteria:

Handability—the resultant composition should: (a) be a single cohesive bolus; (b) be able to be handled and manipulated with minimal to no material transfer (sticking) to latex gloved hand; (c) be able to be handled without material crumbling or falling apart; and (d) exhibit minimal cracking or "tearing" with extreme manipulation, e.g., hard squeezing; and Robustness—the resultant composition, after being placed or injected into or onto the desired location, should be able to withstand body fluids, reasonable irrigation fluids and/or suctioning with minimal material erosion, disintegration or dissolution.

Preferred Embodiment 3

A paste bone graft substitute composition having the following preferred formulation: 100 parts by weight of medical grade calcium sulfate hemihydrate (MGCSH), 1.2 parts by weight of carboxymethylcellulose (CMC), and 31 parts by weight of sterile water.

The preferred method for mixing this putty bone graft substitute composition comprises the following steps: (1) dry blend the powder components (i.e., the calcium WAS sulfate hemihydrate, and carboxymethylcellulose); (2) add the sterile water; and (3) mix or stir all components for approximately 30 seconds to one minute or until the desired putty-like consistency is achieved.

The resultant paste bone graft substitute composition has the following characteristic/criteria:

Ejectability—the resultant composition should be able to be ejected through a ⅛ inch (0.3175 centimeter) diameter orifice with relatively little pressure required.

Preferred Embodiment 4

A bone graft substitute composition having the following preferred formulation: approximately 80-120 parts medical grade calcium sulfate hemihydrate by weight; approximately 21-250 parts sterile water by weight; and approximately 1-40 parts sodium carboxymethylcellulose by weight. This preferred formulation may include approximately 10-100 parts demineralized bone matrix by weight.

The preferred method for mixing this bone graft substitute composition comprises the following steps: (1) dry blend the powder components (i.e., the calcium sulfate hemihydrate, and sodium carboxymethylcellulose, and, if included, the demineralized bone matrix); (2) add the sterile water; and (3) mix or stir all components for approximately 30 seconds to one minute or until the desired consistency is achieved.

The resultant bone graft substitute composition has the following characteristic/criteria:

Handability—the resultant composition should: (a) be a single cohesive bolus; (b) be able to be handled and manipulated with minimal to no material transfer (sticking) to latex gloved hand; (c) be able to be handled without material crumbling or falling apart; and (d) exhibit minimal cracking or "tearing" with extreme manipulation, e.g., hard squeezing;

Ejectability—the resultant composition should: (a) be able to be easily manipulated, e.g., rolled into a long cylinder or other suitable shape, so as to be manually placed into an appropriate injection apparatus, e.g., a syringe; and (b) be able to be ejected through a ⅛ inch (0.3175 centimeter) diameter orifice with relatively little pressure required; and Robustness—the resultant composition, after being placed or injected into or onto the desired location, should be able to withstand body fluids, reasonable irrigation fluids and/or suctioning with minimal material erosion, disintegration or dissolution.

Tests

The majority of tests done to date on the bone graft substitute composition of the present invention basically consist of mixing a specific formulation and then assessing and recording the mixing, handling, consistency, and injectability properties of the resultant material.

Formulation Tests

Injectable Bone Graft Substitute Composition: Formulations with various types and amounts of carboxymethylcellulose and demineralized bone matrix have been tested. Specific examples include: (1) carboxymethylcellulose percentages of 1-10% by weight; (2) types of carboxymethylcellulose have included high viscosity, medium viscosity, and low viscosity from 3 vendors (e.g., Aqualon® 7HF PH sodium carboxymethylcellulose from Hercules Incorporated, Hercules Plaza, 1313 North Market Street, Wilmington, Del. 19894-0001); (3) carboxymethylcellulose sterilized by gamma or electronic beam sterilization (medium and low doses); (4) demineralized bone matrix percentages up to 65% by volume; (5) differently processed demineralized bone matrix, air dried and freeze dried; (6) demineralized bone matrix from two vendors (e.g., human freezed dried demineralized bone matrix from AlloSource, 8085 E. Harvard Ave., Denver, Colo. 80231); and (7) animal demineralized bone matrix, including bovine and canine.

For all these formulations, varying amounts of water, between 31-200 parts by weight, have been tested. The mixing, handling, consistency, and injectability properties were assessed and formulas chosen such that they met the mixing, handability, ejectability, and robustness characteristics/criteria stated hereinabove.

Paste And Putty Bone Graft Substitute Composition: These were the first tests done and included formulations with compositions having 100 parts by weight medical grade calcium sulfate hemihydrate, and between 1-10% by weight carboxymethylcellulose, and between 31-200 parts by weight water. As was the case with the injectable bone graft substitute composition, mixing, handability, consistency, injectability, and robustness properties were assessed for the different formulations. Specific tests have included: (1) varying the carboxymethylcellulose percentages from 0.25% up to 10% by weight, (2) using inorganic salt solutions including 2% sodium chloride (NaCl) by weight, 2-4% sodium sulfate ($Na_2SO_4$) by weight, and 2% potassium chloride (KCl) by weight.

As with the injectable bone graft substitute composition, varying amounts of water, 31-200 parts by weight, were used.

EXAMPLE 1

The osteoinductive properties of the injectable bone graft substitute composition have been studied using an athymic mouse-intramuscular implantation model. This animal model is widely accepted as the "gold standard" for assessing osteoinductive characteristics of bone graft materials. In this model, a given amount of material is surgically placed into a muscular site. After an implantation period of four weeks, the osteoinductive response is assessed using various analytical methods, including radiography, biochemical analysis (alkaline phosphatase levels and calcium content), and histomorphometry.

In this study, four athymic (nude) male mice (Harlan Sprague Dawley, Inc.) were used for each material group. Two muscle pouches were formed in the right and left gluteal muscles of each mouse and implanted with either: 1) pellets which were manufactured using the composition given in Preferred Embodiment 1, or 2) twenty (20) mg of demineralized bone matrix which had been rehydrated with isotonic saline (0.9% NaCl). The pellets made from Preferred Embodiment 1 were 3.0 mm in diameter, 2.5 mm in height and 25 mg in weight.

After twenty-eight (28) days the animals were sacrificed and the materials explanted. The explants were analyzed for osteoinductive potential by assessing the alkaline phosphatase activity and for new bone growth by histomorphometric analysis of histologic sections.

Samples to be analyzed for alkaline phosphatase activity were minced, sonicated, and extracted with water saturated butanol. The extracts were assayed for protein content using a Pierce BCA Protein Assay Kit (Pierce Chemical Co.) and measuring the conversion of para-nitrophenylphosphate (pNPP) to para-nitrophenol (pNP) with time. The results were expressed as umole pNP formed/min/ug tissue protein.

Samples intended for histomorphometric analyses were prepared using standard histological procedures. The percent viable bone (new bone formation) was quantitated employing computer software (Adobe Photo Shop 3.0.4 and HNIH 1.61), in conjunction with a microscope equipped with a video camera. Data was reported as percent viable bone relative to the total cross-sectional area analyzed.

The alkaline phosphatase levels (umole pNP formed/min/ug tissue protein) and percent viable bone results for the groups of mice implanted with DBM only and with injectable putty manufactured using the composition given in Preferred Embodiment 1 are shown in Table 1.

TABLE 1

Osteoinductive Results
Alkaline Phosphatase Levels and Percent Viable Bone

| Group | Alkaline Phosphatase Levels (umole pNP formed/min/ug tissue protein) | Percent Viable Bone (%) |
|---|---|---|
| DMB only | $2.1 \times 10^{-5} \pm 0.3 \times 10^{-5}$ | $6.5 \pm 1.0\%$ |
| Injectable Putty (Preferred Embodiment 1) | $3.0 \times 10^{-5} \pm 0.2 \times 10^{-5}$ | $4.7 \pm 0.9\%$ |

EXAMPLE 2

A study was performed on canines to evaluate healing of bone defects using materials with the composition given in Preferred Embodiment 1. The DBM used in these compositions was fresh frozen canine DBM (Veterinarian Transplant Services, Seattle, Wash.). Two methods were used to produce the test materials. The first material group consisted of a blend of DBM, calcium sulfate, and CMC powder that was irradiated sterilized, while the second group mixed canine DBM with the calcium sulfate-CMC blend at the time of surgery.

In this canine animal model, large medullary cylindrical defects (13 mm diameter×50 mm length) were created bilaterally in the proximal humeri by drilling axially through the greater tubercle. Six to 7 cc of test material were injected into prepared cavities using a large-bore catheter-tip syringe. Left humeri received the premixed material that hand been sterilized and the right humeri received the material mixed intraoperatively which utilized non-irradiated canine DBM. Radiographs of the humeri were obtained preoperative, immediately postoperative, and at 2, 3, and 6 weeks. Following euthanasia after 6 weeks, the explanted humeri were sectioned transversely, radiographed, and processed for plastic imbedded undecalcified histology. The histologic sections were stained with basic fuchsin and toluidine blue and examined by light microscopy.

Post-operative radiographs revealed all test materials to be well contained in the prepared cavities. Normal would healing occurred and there were no postoperative infections. Serial clinical radiographs showed a progressive decrease in materials density with time. no difference was evident between the right and left sides.

Contact radiographs of the cut sections demonstrated no difference in pattern or density of bone filling the right and left defects, non-irradiated and irradiated canine DBM materials groups, respectively. Serial sections for all the dogs showed between 30-100% filling of the defect, with one dog showing almost complete filling for all sections.

Histologically, the nature of new bone formation and the amount of residual material were similar in the right and left defects. In the peripheral one-third of the defects, new bone was present at the margins and haversian surfaces of abundant DBM particles. Residual calcium sulfate was evident, incorporated within slender bone trabeculae, independent of DBM particles. New bone formation in the central aspect of the defects was more variable, with some vascular fibrosus tissue shown. No foreign body or inflammatory response was seen in any of the slides, indicating that the materials had extremely good biocompatibilty.

Thus, materials with compositions given in Preferred Embodiment 1 were shown to be well tolerated by the bone and to heal a large medullary defect 30-100% at six weeks with viable new bone in a canine bone defect model.

Although the present invention has been described and illustrated with respect to preferred embodiments and preferred uses therefor, it is not to be so limited since modifications and changes can be made therein which are within the full intended scope of the invention.

The invention claimed is:

1. A bone graft substitute composition comprising:
    (a) calcium sulfate;
    (b) a mixing solution;
    (c) a cellulose derivative plasticizing agent; and
    (d) demineralized bone.

2. The bone graft substitute composition of claim 1, comprising approximately 40% demineralized bone matrix by dry weight.

3. The bone graft substitute composition of claim 1, wherein the mixing solution is selected from a group consisting of sterile water, an inorganic salt, and a cationic surface active agent.

4. The bone graft substitute composition of claim 3, wherein the cationic surface agent is selected from a group consisting of sodium chloride, phosphate buffered saline, potassium chloride, sodium sulfate, ammonium sulfate, ammonium acetate, and sodium acetate.

5. The bone graft substitute composition of claim 1, wherein the mixing solution comprises sterile water.

6. The bone graft substitute composition of claim 1, wherein the cellulose derivative is selected from a group consisting of sodium carboxymethylcellulose, methylcellulose, hydroxypropyl methylcellulose, ethylcellulose, hydroxyethylcellulose and cellulose acetate butyrate.

7. The bone graft substitute composition of claim 1, wherein the cellulose derivative comprises carboxymethylcellulose.

8. The bone graft substitute composition of claim 1, wherein the calcium sulfate comprises calcium sulfate hemihydrate.

9. The bone graft substitute composition of claim 1, wherein the calcium sulfate comprises calcium sulfate hemihydrate, the mixing solution comprises sterile water, and the cellulose derivative comprises carboxymethylcellulose.

10. The bone graft substitute composition of claim 9, comprising approximately 100 parts calcium sulfate hemihydrate by weight, approximately 11.1 parts carboxymethylcellulose by weight, approximately 162 parts water by weight, and approximately 69.4 parts demineralized bone matrix by weight.

11. A bone graft substitute composition comprising:
    (a) approximately 80-120 parts medical grade calcium sulfate hemihydrate by weight;
    (b) approximately 21-250 parts sterile water by weight;
    (c) approximately 1-40 parts carboxymethylcellulose by weight; and
    (d) approximately 10-100 parts demineralized bone matrix by weight.

12. The bone graft substitute composition of any one of claims 1 to 11, further comprising a bone allograft.

13. A method of making a bone graft substitute composition, the method comprising: providing a first composition comprising calcium sulfate, a cellulose derivative plasticizing agent and demineralized bone matrix; and contacting the first composition with a mixing solution to form the bone graft substitute composition.

14. The method of claim 13, wherein the first composition further comprises a bone allograft.

15. The method of claim 13, further comprising forming the bone graft substitute composition into a putty.

16. The method of claim 13, wherein the calcium sulfate comprises calcium sulfate hemihydrate, the cellulose derivative comprises carboxymethylcellulose, and the mixing solution comprises sterile water.

* * * * *